(12) United States Patent
Martini

(10) Patent No.: US 6,168,601 B1
(45) Date of Patent: Jan. 2, 2001

(54) LOCK REDUCTION DEVICE AND METHOD

(76) Inventor: Giuseppe Martini, Via Filippo Maria Renazzi, N°4/a - 000165 Rome (IT)

( * ) Notice: Under 35 U.S.C. 154(b), the term of this patent shall be extended for 0 days.

(21) Appl. No.: 09/312,521

(22) Filed: May 14, 1999

(51) Int. Cl.[7] .................................................. A61B 17/66
(52) U.S. Cl. .............................. 606/90; 600/237; 433/140
(58) Field of Search ............................ 433/140; 600/237, 600/238, 239, 243, 244; 606/90, 174, 205, 208

(56) References Cited

U.S. PATENT DOCUMENTS

| | | | |
|---|---|---|---|
| 1,918,889 | * | 7/1933 | Bacon ................................... 600/207 |
| 2,075,534 | * | 3/1937 | McCormack ........................... 600/219 |
| 2,291,413 | * | 7/1942 | Siebrandt .............................. 606/103 |

\* cited by examiner

Primary Examiner—Michael Buiz
Assistant Examiner—David O. Reip
(74) Attorney, Agent, or Firm—Foley & Lardner

(57) ABSTRACT

A device for distracting a temporomandibular joint and repositioning an antetiorly dislocated disc in a patient comprises upper and lower elongated members coupled together by a pivotal, slidable and releasable coupling. This versatile coupling is accomplished by providing the upper member with a longitudinally extending cavity and the lower member with a roller configured for translation within the cavity. Each member includes a handle at one end and an opposite distal tip configured for engaging posterior teeth of the upper and lower jaws. The lower member includes a clamp for adjustably securing the patient's mandible to the lower member. A method of using the device comprises positioning the device in the patient's mouth so that the distal tips are seated on upper and lower posterior teeth of the patent, squeezing the handles together to distract the joint, and sliding the lower member anteriorly (toward the opening of the mouth) relative to the upper member.

20 Claims, 4 Drawing Sheets

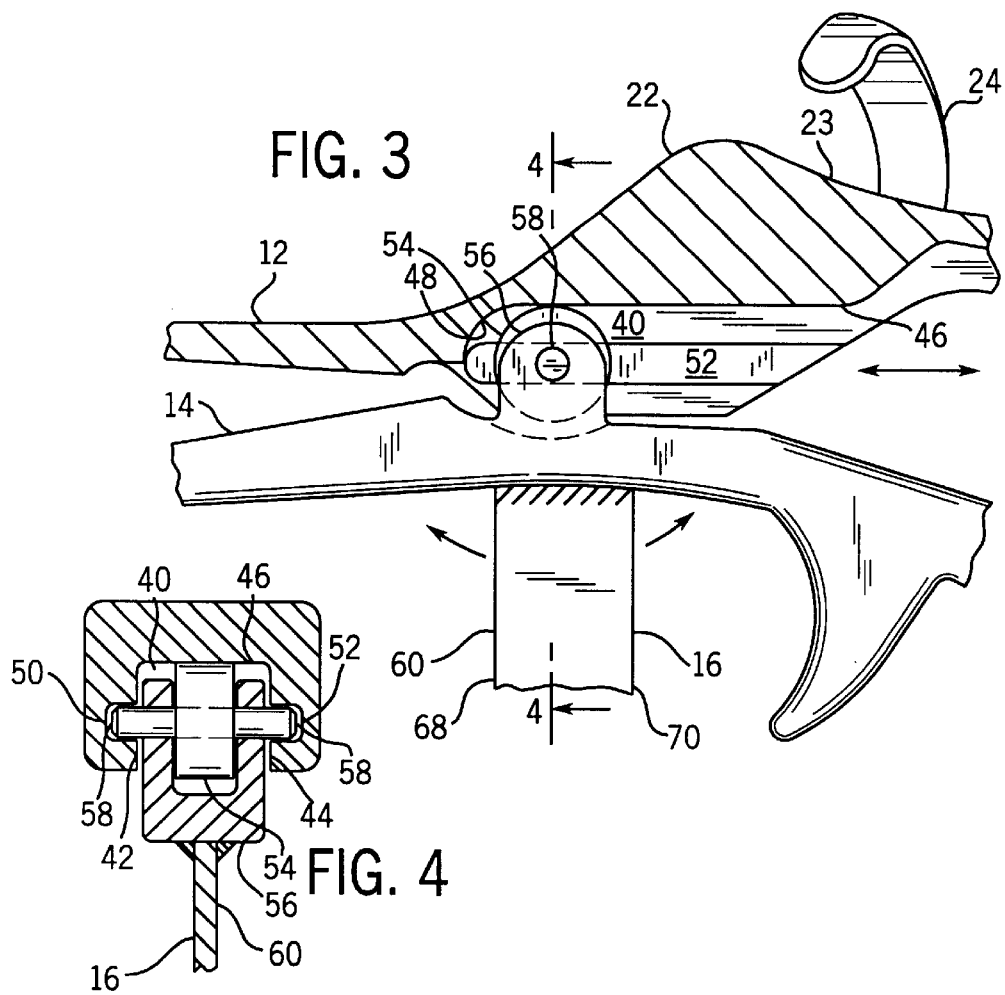
FIG. 3
FIG. 4
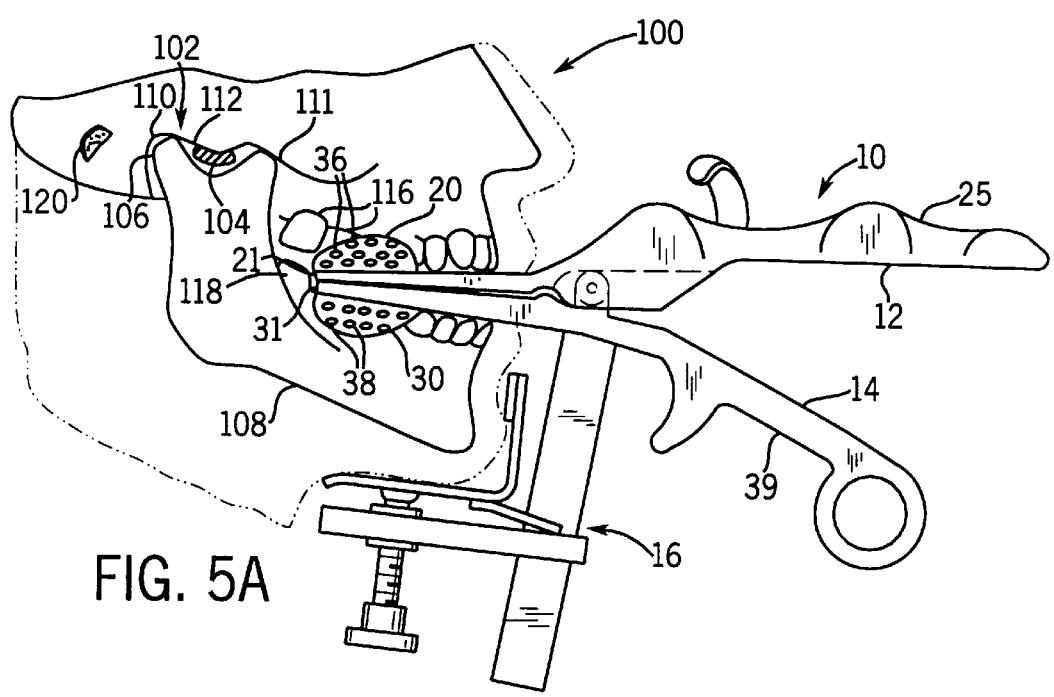
FIG. 5A

LOCK REDUCTION DEVICE AND METHOD

FIELD OF THE INVENTION

The present invention relates to mechanical devices for manipulating temporomandibular joints and, more particularly, to devices for reducing or repairing dysfunctional disturbances of the masticatory system. Specifically, this invention relates to an instrument useful for reestablishing a normal or improved condyle-disc-fossa relationship in patients with an anteriorly dislocated disc. The invention also includes a method of using the instrument to reestablish the normal condyle-disc-fossa relationship.

BACKGROUND OF THE INVENTION

The temporomandibular joint is a compound multiaxial joint constructed to permit different types of movement (hinge and glide articulation) of the mandible and different degrees of mouth opening. This is made possible by the presence of an articular disc (or meniscus) interposed between the condyle of the mandible and the glenoid (or mandibular) fossa of the temporal bone. The articular disc divides the joint into an upper (glenoid fossa-disc) and a lower (condyle-disc) compartment. In the normal relation, the condyle sits in the articular fossa with its anterior-superior surface closely approximating the posterior-inferior surface of the articular eminence of the temporal bone. A thin portion of the disc rests between the two surfaces, and a thickened portion of the disc rests at the superior angle of the condyle.

Normally, when the jaws are closed, the condyle contacts the disc and the disc contacts the glenoid fossa. If contact is maintained between the upper and lower teeth while gliding movements are performed, this contact relationship should be maintained. During opening movements, a smooth gliding relationship between the upper and lower compartments of the joint should also be maintained. The first phase in mouth opening is a simple hinge action, which involves only the lower (condyle-disc) compartment of the joint. Specifically, it consists of the condyle head rotating around a point on the under surface of the disc, while the body of the mandible drops almost passively downward and backward.

The second phase in mouth opening involves the lower and upper compartments of the joint and consists of a gliding of the condyle and disc forward and downward along the articular eminence. This occurs alone during protrusion and lateral movements of the mandible and in combination with the hinge action during the wider opening of the mouth. A wide opening of the mouth would be impossible with a simple hinge movement since the posterior surface of the ramus would compress the soft tissue between the mandible and the mastoid process. The gliding action brings the ramus forward and also downward so that the hinge action can continue.

Several types of temporomandibular joint dysfunctions can reduce or prevent a wide opening of the mouth. One common joint dysfunction is known as an anteriorly dislocated disc—also known as a posterior condylar displacement. In the temporomandibular joint, the space posterior to the condyle is filled with fibrous tissue that is compressible. The posterior attachment of the superior head of the external pterygoid muscle is posterior on the neck of the condyle. This attachment can stretch or "break down" along with the tight lateral and medial fibers attaching disc and condyle, thus allowing the disc to slide anteriorly on the condyle. If the disc slides anteriorly to the point that the thick portion of the disc rests on the anterior-superior surface of the condyle—instead of its normal resting position on the superior angle of the condyle—this condition is known as a complete anterior dislocation of the disc or a lodged disc.

In patients with a complete anterior dislocation of the disc, the range of condylar translation is limited by the anteriorly dislocated disc on the affected side. This condition often progresses from intermittent locking to acute locking, which usually becomes permanent. A lodged disc forces the condyle to "slip or snap" over the thickened portion of the disc, which may thicken even further as the condition becomes more chronic due to folding of the disc. Thus, the patient experiences a "click" as the teeth are occluded because the condyle is displaced posteriorly but the disc is not, and another "click" occurs as the patient's mouth is opened and the structures regain their normal relations.

A known technique for reducing an anteriorly dislocated disc involves manually manipulating the jaw in an effort to assist the patient to unlock his or her jaw. This is accomplished by an operator or clinician simultaneously pushing down on the lower posterior teeth while pulling up on the patient's chin. This maneuver is designed to distract the joint. During the first part of the maneuver the mandible must be kept in a retruded (or rearward) position. Importantly, the mandible must never be forcibly pulled forward or forcibly opened unless the joint is also being distracted, as this could damage the joint.

Keeping the mandible in a retruded position, the operator continues to press downward on the posterior teeth and pull up on the chin. After a few moments, the patient is instructed to move the jaw from side to side, concentrating on moving it toward the side opposite the dislocated disc. While the joint is being distracted and the operator and patient are moving the jaw to the opposite side, the disc will hopefully snap back into place. Although this can sometimes be felt or heard, in some instances there is no noise or other physical evidence that the disc has been repositioned other than the return of full range of lateral movement to the opposite side of the jaw.

After the dislocated joint has been reduced (or the range of movement to the opposite side increased), the patient is instructed to not close the teeth together until a mouth prop can be inserted, which will maintain the mandible in an open position. After keeping the mandible in the open position for about fifteen minutes, the mouth prop is removed and replaced with a repositioning splint (or bite plane). This splint is prepared ahead of time and typically has an extremely large flange extending downward anteriorly to engage the lingual surfaces of the lower cuspids, bicuspids, and incisors so that the patient cannot retrude the mandible when it is near the closed jaw position. The splint will typically maintain the mandible forward of its previous intercuspal position by about 3 mm to 5 mm. The splint remains in place for twenty-four hours a day for at least two weeks, except for brief occasions when the splint is removed for cleaning and brushing of the teeth, during which the mouth prop is used to maintain the jaw in the open position. This period of at least two weeks during which the patient's jaw is maintained in the open position gives the disc a chance to heal.

The present invention provides a device that facilitates the operator in distracting the temporomandibular joint and reestablishing the proper condyle-disc-fossa relationship. The device is advantageous in that permits the operator to more accurately control both the direction and magnitude of forces applied to the patient's mandible than is possible by hand manipulations alone. Another marked advantage of the device is it substantially reduces the risk of the mandible being forcibly pulled forward or forcibly opened unless the joint is also being distracted.

SUMMARY OF THE INVENTION

This invention provides a device for distracting a temporomandibular joint in a patient. The device comprises first and second elongated members movably coupled together. Each member includes a handle at one end and an opposite distal tip configured for engaging teeth of the upper or lower jaws. In a preferred form of the invention, the movable coupling is a pivotable, slidable, and releasable coupling. In another preferred form of the invention, the second member includes a clamp for adjustably securing the patient's mandible to the second member.

The invention also provides a device for repositioning an anteriorly dislocated disc in a temporomandibular joint of a patient. The device comprises upper and lower members movably coupled together. The upper member includes a handle at one end and an upwardly facing surface at an opposite end configured for engaging posterior teeth of the patient's upper jaw. The lower member includes a handle at one end and a downwardly facing surface at an opposite end configured for engaging posterior teeth of the patient's lower jaw. In a preferred form of the invention, the movable coupling is a pivotable, slidable, and releasable coupling. In another preferred form of the invention, the lower member includes a clamp for adjustably securing the patient's mandible to the lower member.

The invention further provides a method of using the device to distract a temporomandibular joint and reposition an anteriorly dislocated disc in a patient. The method comprises steps of positioning the device in the patient's mouth so that the distal tips of the elongated members are seated on upper and lower posterior teeth of the patent, squeezing the handles together to distract the joint, and sliding the lower member anteriorly (toward the opening of the mouth) relative to the upper member to reestablish the desired condyle-disc-fossa relationship. A repositioning splint may be placed in the patient's mouth after the device is removed to maintain the jaw in an open position while the disc heals.

These and other benefits and features of the invention will be apparent upon consideration of the following detailed description of preferred embodiments thereof, presented in connection with the following drawings in which like reference numerals identify like elements throughout.

BRIEF DESCRIPTION OF THE DRAWINGS

FIG. 3 is an enlarged, partial-side-sectional view of a central portion of the device of FIG. 1.

FIG. 4 is a front, cross-sectional view of the central portion of the device of FIG. 1 taken along line 4—4 in FIG. 3.

FIG. 5A is a schematic representation showing the device of FIG. 1 being positioned in the jaw of a patient suffering from a complete anterior dislocation of the disc.

DETAILED DESCRIPTION OF THE PREFERRED EMBODIMENTS

Figure 1:
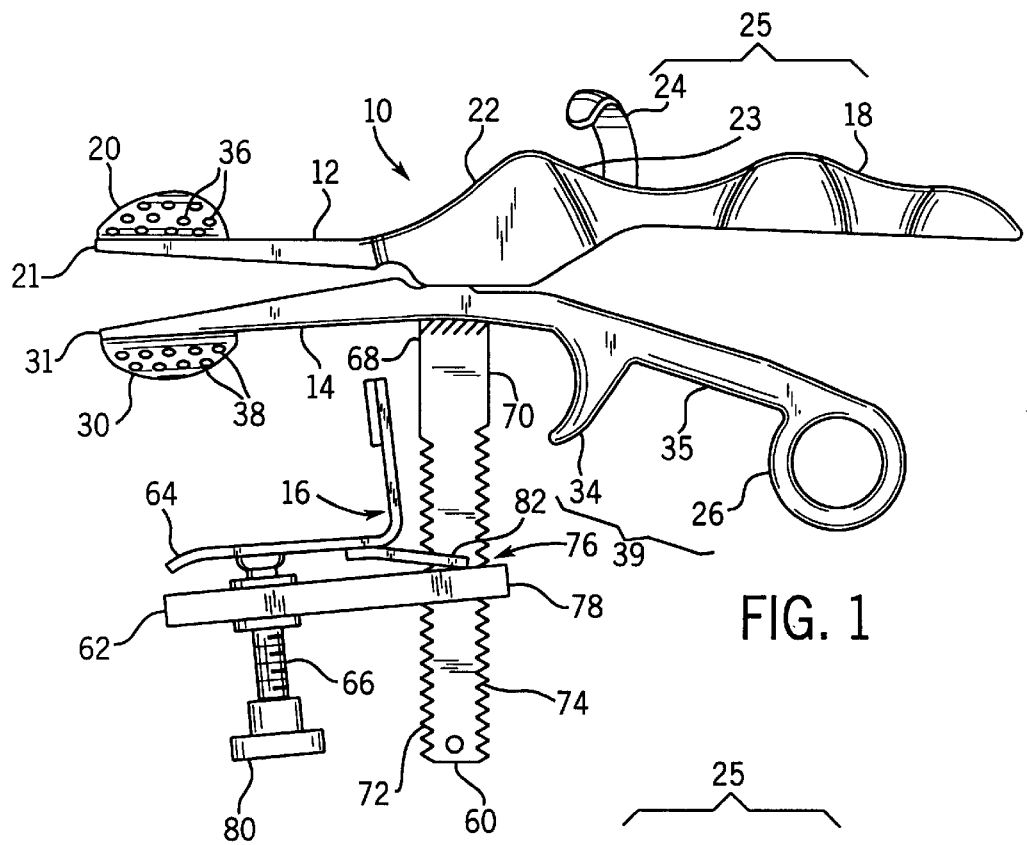
FIG. 1 is side elevation view of a device in accordance with the present invention.
Figure 2:
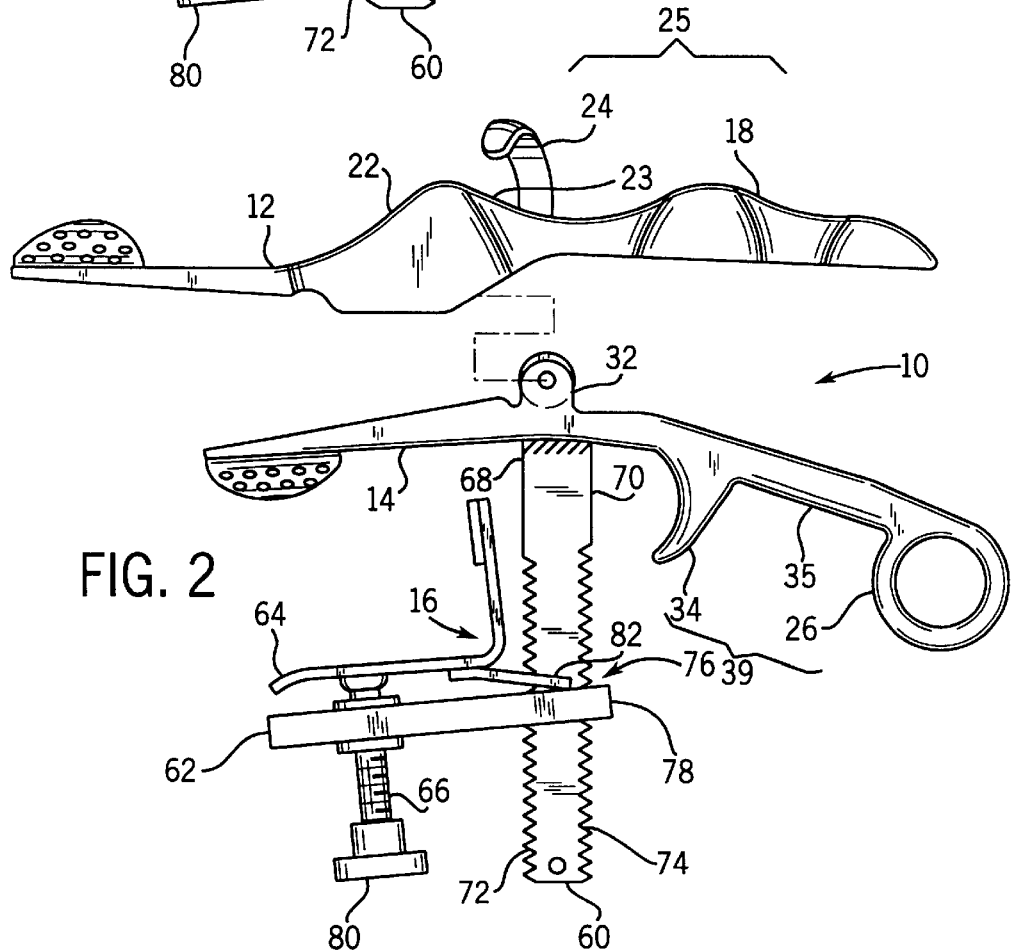
FIG. 2 is a partially exploded view of the device of FIG. 1.

As shown in FIGS. 1 and 2, a preferred embodiment of a device or instrument 10 used to facilitate the repositioning of an anteriorly dislocated disc in a temporomandibular joint of a patient comprises upper and lower elongated members 12, 14 and a mandibular (external) clamp 16. Upper member 12 includes a contoured palm grip 18 at one end, a receptacle 20 at an opposite distal tip 21, and a centrally located housing 22 and thumb catch 24. A surface 23 of housing 22 provides a convenient stop for the operator's thumb. Palm grip 18, thumb-stop 23 and thumb catch 24, taken together, define a handle 25 of upper member 12.

Lower member 14 includes a little-finger grip 26 at one end, a receptacle 30 at an opposite distal tip 31, and a centrally located roller 32 and forefinger rest 34. A tubular portion 35 of member 14 intermediate little-finger grip 26 and forefinger catch 34 provides an area that is grasped by the operator's middle and index fingers. Receptacles 20 and 30 face in opposite directions and are configured for engaging the upper and lower posterior teeth, respectively, of the patient. Preferably, receptacles 20, 30 include perforations 36, 38, respectively, the purpose of which is described below. Little-finger grip 26, tubular portion 35 and forefinger catch 34, taken together, define a handle 39 of lower member 14.

As best seen in FIGS. 3 and 4, upper member 12 is configured to releasibly, slidably and pivotally couple with lower member 14. This versatile coupling arrangement is accomplished by providing housing 22 of upper member 12 with a longitudinally extending cavity 40 configured to receive roller 32 of lower member 14. As best seen in FIG. 4, cavity 40 of upper member 12 is defined by a pair of vertical side walls 42, 44, a horizontal top wall 46, and a curved front wall 48. Thus, cavity 40 is preferably open to the bottom and the rear. Cavity 40 also includes a pair of opposed rails 50, 52 that extend longitudinally along respective side walls 42, 44 from curved front wall 48 to the open rear of cavity 40. Roller 32 of lower member 14 comprises a wheel 54 rotatably supported within an axle support 56 on an axle 58, which protrudes laterally from both exterior side surfaces of axle support 56. As best seen in FIG. 4, axle 58 and axle support 56 are configured such that the lateral protrusions of axle 58 slidably ride in opposed rails 50, 52 of cavity 40 whenever upper member 12 is coupled with lower member 14. As can also be seen, wheel 54 is configured to ride along top wall 46 of cavity 40 whenever members 12 and 14 are coupled together.

As will be evident to one of ordinary skill in the art, the foregoing coupling arrangement between the two members 12 and 14 permits relative pivoting movement about axle 58. In addition, the coupling arrangement permits the two member 12 and 14 to move longitudinally relative to one another with good lateral stability and smooth travel. Moreover, the coupling arrangement also permits the two members 12 and 14 to be easily separated from one another, which facilitates cleaning of instrument 10. In addition, upper and lower members 12, 14 are preferably made of stainless steel, which also facilitates cleaning.

Returning now to FIGS. 1 and 2, clamp 16 comprises a blade 60, a slide bar 62, a chin support 64, and an adjustable thumb screw 66. Preferably, blade 60 is fixedly attached (e.g., welded) to lower member 14 and extends generally perpendicularly thereto from a location directly beneath roller 32. Blade 60 includes front and rear edges 68, 70 provided with teeth 72, 74, respectively. Slide bar 62 preferably includes a slot 76 that is long enough to allow bar 62 to be easily moved vertically along blade 60 whenever bar 62 is held in a substantially perpendicular orientation relative to blade 60, but short enough to cause the front and rear edges of slot 76 to engage teeth 72, 74 (and thereby lock bar 62 in place) whenever bar 62 is not substantially perpendicular to blade 60. In addition, slot 76 is preferably located close to an end 78 of bar 62 so that bar 62 automatically assumes a small angle relative to the perpendicular orientation (which thus locks bar 62 in place) due to the weight of bar 62 whenever the operator does not intentionally maintain the perpendicular orientation. Chin support 64 is attached to one end of thumb screw 66 above bar 62, and a knob 80 is attached to the other end of screw 66 below bar 62. Chin support 64 preferably includes a forked extension 82 that engages front edge 68 of blade 60 to maintain support 64 in a desired forward facing relationship when knob 80 and screw 66 are rotated.

As will be evident to one of ordinary skill in the art, the foregoing arrangement of clamp 16 permits bar 62 to be easily slid along blade 60 for making large (or rough) adjustments in the vertical separation between receptacle 30 and chin support 64. In addition, the arrangement permits small (or fine) adjustments in the vertical separation to be made by simply rotating knob 80 in the appropriate direction. Moreover, slide bar 62 can be easily separated from blade 60, which facilitates cleaning of instrument 10. Clamp 16 is preferably made of stainless steel, which also facilitate cleaning.

Figure 5B:
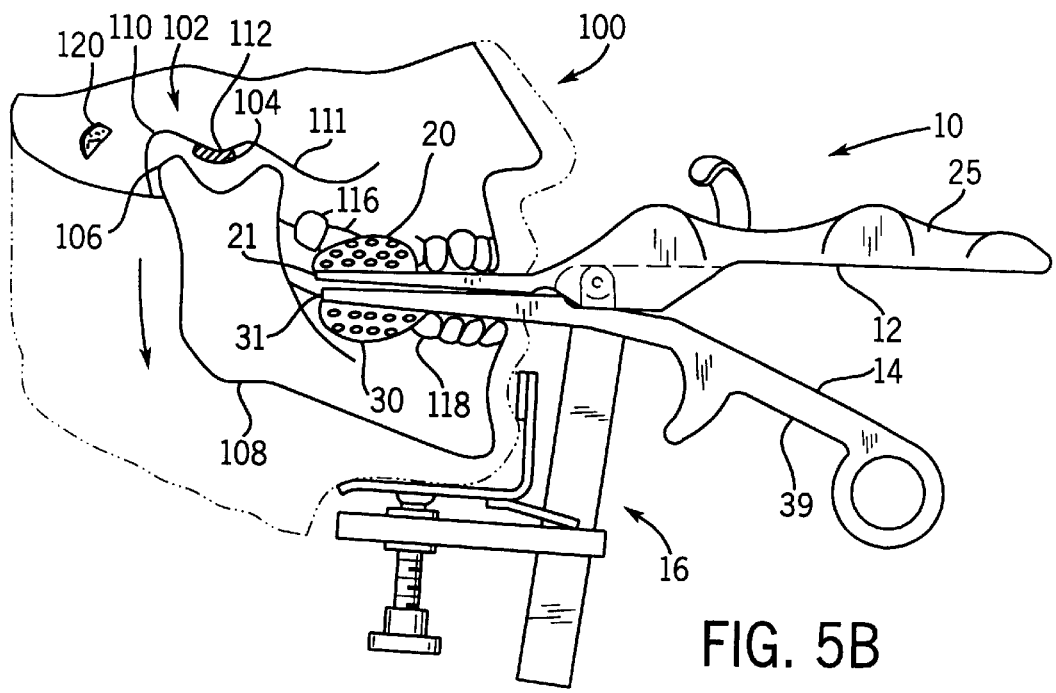
FIG. 5B is a schematic representation similar to FIG. 5A, but showing the device being used to distract the temporomandibular joint and lower the condyle from its normal resting position in the fossa.

Now that instrument 10 has been sufficiently described, a method of using instrument 10 to distract a temporomandibular joint 102 and reposition an anteriorly dislocated disc 104 in a patient 100 will now be described with particular reference to the schematic representations of FIGS. 5A–5D and FIG. 6. As illustrated in FIG. 5A, a condyle 106 of a mandible 108 rests in an articular fossa 110 of a temporal bone 111 such that its anterior-superior surface closely approximates (or even contacts) the posterior-inferior surface of an articular eminence 112. As also illustrated, instead of articular disc 104 being positioned in its normal resting position on the superior angle of the condyle 106, it is positioned on the inferior surface of eminence 112 anteriorly of its normal resting position, i.e., patient 100 has suffered a complete anterior dislocation of disc 104.

In a preferred method of using instrument 10 to reestablish a normal or improved condyle-disc-fossa relationship in patient 100, a pliable thermoplastic resin is softened and placed in receptacles 20, 30 of upper and lower members 12, 14. Instrument 10 is then placed in the patient's mouth on the affected side and a bite registration of upper and lower posterior teeth 116, 118 is established. As the patient bites down (see FIG. 5A), some of the resin will seep out through perforations 36, 38 in receptacles 20, 30. Instrument 10 is then removed from the mouth and the resin is "set" with cool water. The resin that flows through perforations 36, 38 during the bite registration procedure also hardens and ensures that the hardened bite registration will remain securely locked in place for the remainder of the procedure. One of ordinary skill in the art will know of several thermoplastic resin materials suitable for making a bite registration, but one such thermoplastic resin routinely used is KERR PRECISION COMPOUND®. KERR is the U.S. manufacturer of this readily available, green-colored material.

Once the resin has been firmly set in receptacles 20, 30, instrument 10 is returned to the mouth and seated on the posterior teeth 116, 118 previously registered (see FIG. 5A). Mandibular clamp 16 is adjusted for contact with the patient's chin and adjacent lower border of the mandible. The operator's free hand (index and middle finger) is positioned just anterior to the external auditory meatus 120 on the affected side in order to palpate the movement of condyle 106 during the procedure. Handles 25, 39 of instrument 10 are squeezed together in one continuous motion that initially separates distal tips 21, 31 of upper and lower members 12, 14 and subsequently moves lower member 14 in an anterior direction (towards the front of the mouth) relative to upper member 12 (see FIGS. 5B and 5C).

Figure 5C:
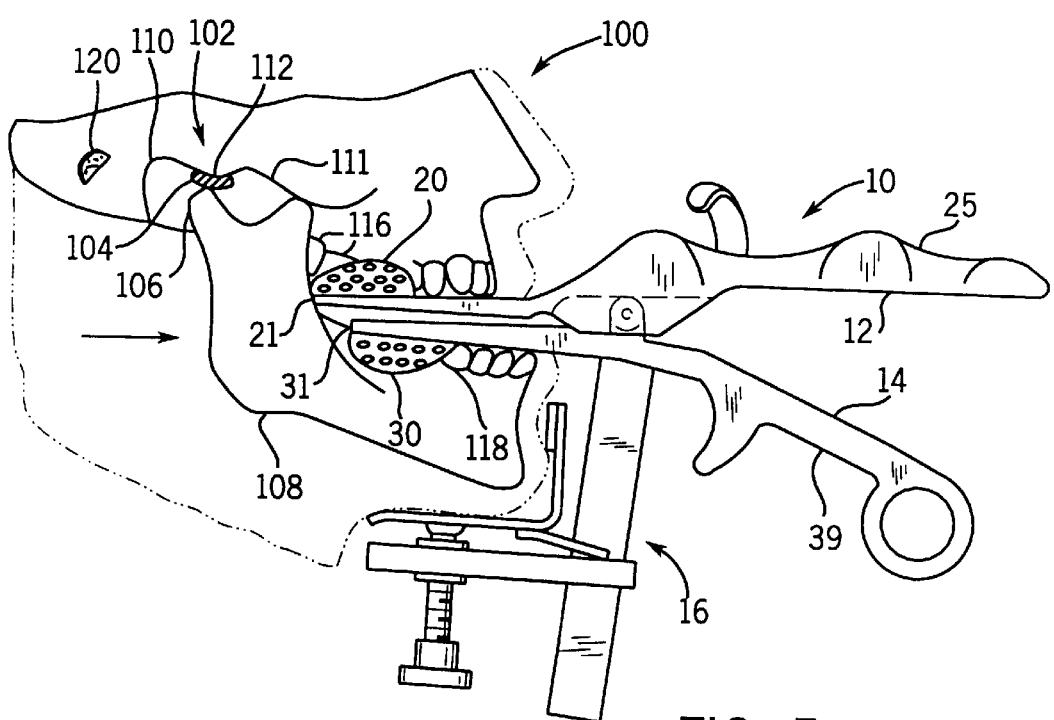
FIG. 5C is a schematic representation similar to FIG. 5B, but showing the device being used to maintain the temporomandibular joint in a distracted position while the mandible and condyle are translated anteriorly.
Figure 5D:
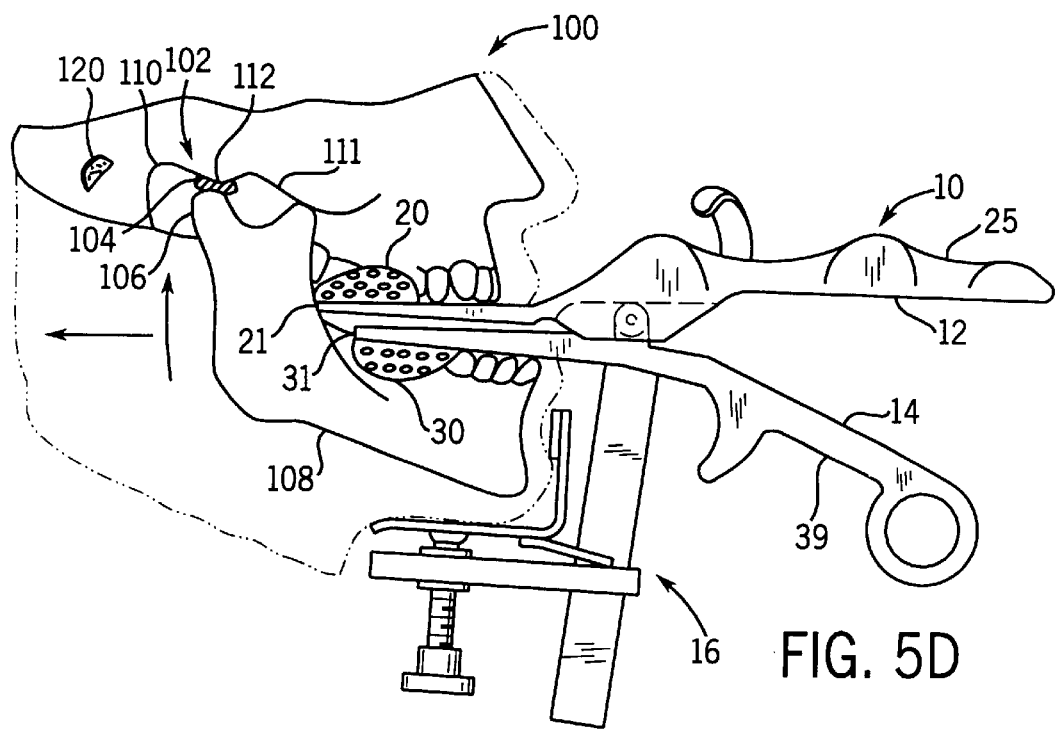
FIG. 5D is a schematic representation similar to FIG. 5C, but showing the device being used to reestablish a normal contact relationship between the condyle and the disc.
Figure 6:
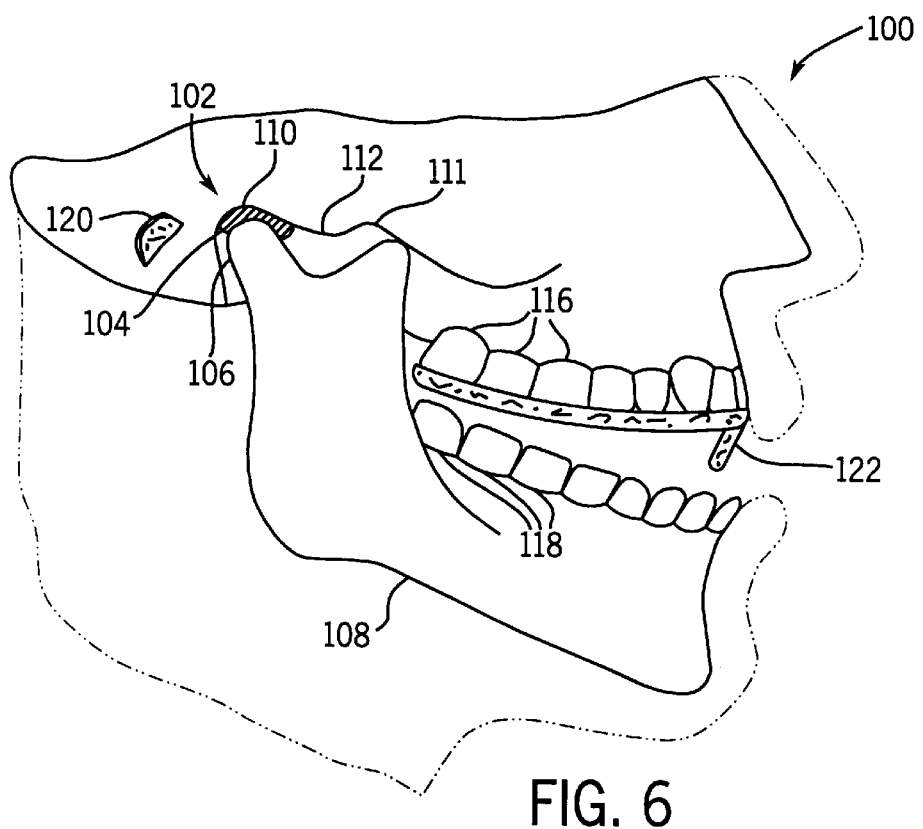
FIG. 6 is a schematic representation similar to FIG. 5D, but showing an anterior repositioning splint being used to maintain the jaw in an open position after the normal condyle-disc-fossa relationship has been reestablished with the device.

As will be evident to one of ordinary skill in the art, the net effect of the above-described action of instrument 10 is to move condyle 106 downward out of fossa 110 and forward onto anteriorly positioned disc 104 (see FIG. 5C). The procedure is concluded by releasing the pressure from handles 25, 39 (see FIG. 5D), loosening exterior clamp 16, and removing instrument 10 from the patient's mouth. Preferably, the mouth is then held open while an anterior repositioning splint 122 is immediately placed in the patient's mouth to ensure that the reestablished condyle-disc-fossa relationship is maintained until the disc heals (see FIG. 6). Splint 122 is an orthodontic device that is well known to those of ordinary skill in the art.

Numerous characteristics, advantages, and embodiments of the invention have been described in detail in the foregoing description with reference to the accompanying drawings. However, the disclosure is illustrative only and the invention is not limited to the precise illustrated and described embodiments. Various changes and modifications may be effected by one skilled in the art without departing from the scope or spirit of the present invention. For example, rather than using a thermoplastic resin to construct a bite registration, one of ordinary skill will know of other suitable non-resin or non-thermosetting materials that could be used.

What is claimed is:

1. A device for distracting a temporomandibular joint of a patient, comprising:

an elongated first member having a handle at one end and an opposite distal tip configured for engaging teeth of an upper jaw; and an elongated second member having a handle at one end and an opposite distal tip configured for engaging teeth of a lower jaw, the second member being pivotally and slidably coupled to the first member, the coupling being configured so that squeezing the handles together while sliding the handles longitudinally relative to each other causes the distal tips to move apart vertically and longitudinally to distract the temporomandibular joint.

2. The device of claim 1, wherein the coupling between the first and second members further permits releasable movement.

3. The device of claim 1, wherein the distal tips are provided with resin material having bite registrations with the teeth of the upper and lower jaws.

4. The device of claim 1, wherein the first member includes a longitudinally extending cavity, and the second member includes a roller configured for translation within the cavity.

5. The device of claim 4, wherein the cavity is partly defined by side walls having rails, and the roller includes laterally extending posts configured to ride in the rails.

6. The device of claim 4, wherein the cavity is partly defined by a top wall, and the roller includes a wheel configured to roll along the top wall.

7. The device of claim 1, wherein the distal tip of the first member is an upwardly facing receptacle, and the distal tip of the second member is a downwardly facing receptacle.

8. The device of claim 7, wherein each receptacle is perforated.

9. The device of claim 1, wherein the handle of the first member includes at least one of a thumb-stop, a thumb catch, and a palm grip.

10. The device of claim 1, wherein the handle of the second member includes at least one of a forefinger catch, a tubular section, and a little-finger grip.

11. A device for distracting a temporomandibular joint of a patient, comprising:
   an elongated first member having a handle at one end and an opposite distal tip configured for engaging teeth of an upper jaw; and
   an elongated second member having a handle at one end and an opposite distal tip configured for engaging teeth of a lower jaw, the second member being movably coupled to the first member,
   wherein the second member includes a clamp configured to adjustably secure a mandible of the patient to the second member.

12. The device of claims 11, wherein the clamp comprises:
   a blade extending generally perpendicularly from the second member, the blade having teeth along front and rear edges;
   an adjustable slide bar configured to slide on the blade; and
   a chin support mounted on the slide bar.

13. The device of claim 12, wherein the chin support is adjustably mounted on the slide bar by a screw.

14. A device for repositioning an anteriorly dislocated disc in a temporomandibular joint of a patient, comprising:
   an elongated upper member having a handle at one end and an opposite end having an upwardly facing surface configured for engaging posterior teeth of an upper jaw; and
   an elongated lower member having a handle at one end and an opposite end having a downwardly facing surface configured for engaging posterior teeth of a lower jaw, the lower member being pivotally and slidably coupled to the upper member, the coupling being configured so that squeezing the handles together while sliding the handles longitudinally relative to each other causes the distal tips to move apart vertically and longitudinally to reposition the anteriorly dislocated disc.

15. The device of claim 14, wherein the coupling between the upper and lower members further permits releasable movement.

16. The device of claim 14, wherein the distal tips are provided with resin material having bite registrations with the teeth of the upper and lower jaws.

17. The device of claim 14, wherein the upper member includes a longitudinally extending cavity, and the lower member includes a roller configured for translation within the cavity.

18. The device of claim 17, wherein the cavity is partly defined by side walls having rails, and the roller includes laterally extending posts configured to ride in the rails.

19. The device of claim 17, wherein the cavity is partly defined by a top wall, and the roller includes a wheel configured to roll along the top wall.

20. The device of claim 14, wherein the lower member includes a clamp configured to adjustably secure a mandible of the patient to the lower member.

* * * * *